United States Patent [19]

Feaster

[11] Patent Number: 5,133,748
[45] Date of Patent: Jul. 28, 1992

[54] INTRAOCULAR LENS FIXATED TO THE CAPSULAR MEMBRANE OR IRIS WITH ADHESIVE

[76] Inventor: Fred T. Feaster, 1125 College Ave., Fort Worth, Tex. 76104

[21] Appl. No.: 657,152

[22] Filed: Feb. 19, 1991

Related U.S. Application Data

[63] Continuation-in-part of Ser. No. 494,760, Mar. 16, 1990, abandoned.

[51] Int. Cl.⁵ .............................................. A61F 2/16
[52] U.S. Cl. .............................................. 623/6
[58] Field of Search .................................... 623/6

[56] References Cited

U.S. PATENT DOCUMENTS 4,504,981  3/1985  Walman ................................ 623/6
4,573,998  3/1986  Mazzocco ............................. 623/6
5,002,571  3/1991  O'Donnell, Jr. et al. ............ 623/6

FOREIGN PATENT DOCUMENTS 0234365A  4/1986  Fed. Rep. of Germany .......... 623/6

Primary Examiner—Ronald Frinks
Attorney, Agent, or Firm—Arthur F. Zobal; Geoffrey A. Mantooth

[57] ABSTRACT

An artificial intraocular lens or optic is attached to the capsular membrane or iris of the eye with adhesive after the human lens is removed or upon removal of a previously implanted artificial intraocular lens. The optic also may be attached to the iris with adhesive with the human lens in place to correct for deficiencies of the eye. The lens implant may have holes or wells for receiving adhesive for attachment purposes.

8 Claims, 6 Drawing Sheets

| | R₁ | R₂ | ABBREVIATION |
|---|---|---|---|
| I | OCH₃ | OCH₃ | DMPA |
| | H | OCH₃ | BME |
| | H | OC₄H₉ | BUME |
| | H | OCH(CH₃)₂ | IME |

II  R = —C(CH₃)₂OH  UVH
    R = —CH(OC₂H₃)₂  DEAP

III  PCH

IV  PPO

V  PDO

VI  R = H  BP

VII
- R = —CH₃  MTX
- R = —C(CH₃)₃  TBTX
- R = —CH(CH₃)₂  ITX
- R = —(CH)₁₁—CH₃  DTX
- R = —OCH₂COOH  CMTX
- R = Cl  CTX

INTRAOCULAR LENS FIXATED TO THE CAPSULAR MEMBRANE OR IRIS WITH ADHESIVE

This application is a continuation-in-part of U.S. patent application Ser. No. 07/494,760, filed on Mar. 16, 1990 now abandoned.

BACKGROUND OF THE INVENTION

1. Field of the Invention

The invention relates to an intraocular lens implant device for placement within the human eye for restoration of vision after the removal of an extra capsular cataract.

2. Description of the Prior Art

There have been many different intraocular lens designs and styles which incorporate and rely upon on many different principles and methods for fixation within the eye. The first modern intraocular lens implanted in 1949 by Mr. Ridley was placed within the capsular bag and relied on posterior capsular fixation, peripherally, for support. Additional support was obtained by iridocapsular adhesions which developed naturally postoperatively as a result of the inflammation produced by the cataract surgery. The problem with this particular design, however, was that fixation was unreliable since the iridocapsular adhesions were unpredictable in their development postoperatively.

Since this first implant design, many other fixation principles have been utilized including:

1. Anterior chamber angle fixation.
2. Pupillary support.
3. Iris Fixation
    A. Iris suture
    B. Iris clip
4. Iridocapsular fixation
5. Scleral fixation
    A. Anterior chamber Posterior Chamber
    B. Ciliary sulcus fixation—Shearing style
    C. Capsular bag fixation In the anterior chamber design, fixation is accomplished by peripheral haptic members that extend into the angle of the anterior. The iris clip and iris suturing techniques employ the use of a clip or iris suture to hold the implant to the iris.

In the posterior chamber, ciliary sulcus fixation is accomplished again by a peripheral haptic member which extends beyond the optic, and accomplishes fixation by contacting the peripheral tissues of the eye posterior to the iris in the area of the ciliary sulcus.

Posterior chamber fixation within the capsular bag is accomplished by several implant designs. All of the designs require haptic members which extend peripherally from the optic into the capsular cul-de-sac and thereby hold the implant in place. Sometimes adhesions develop in the area of the "cul-de-sac", where the anterior capsular surface curves around its equatorial transition to become the posterior capsule. Some designs simply wedge themselves into position in this peripheral capsular cul-de-sac and, in fact, never develop true adhesions, and are simply fixated by physical pressure in the peripheral capsular cul-de-sac. Other implant designs are held in position by adhesions developing between the anterior and posterior capsule around the peripheral haptic member. In most cases, it is felt that no true adhesion develops between the haptic and the capsule itself or the optic in the capsule itself, but that the implant is fixated and held in position due to capsular adhesions developing between the anterior and posterior capsules, these adhesions developing around, but not onto, the peripheral fixation members. This lack of adhesions directly to the peripheral haptic member is evidenced also by the relatively easy removal of many implants, the haptics of which can slide through tunnels composed of surrounding adhesive tissue.

In one particular design, the posterior surface of the "wings" peripheral to the central optic have been roughened to produce an opacifiction of these "wing" portions of the lens adjacent to the central optic. This is to eliminate glare from the optic edge. It has been claimed that this style fixates well not only due to peripheral haptic adhesions within the capsular bag, but possibly due also to capillarity or adhesions developing between the roughened posterior surface of the optic "wings".

As mentioned, all of the above designs within the capsular bag are dependent upon either biologically developing capsular adhesions around peripheral haptics, or the implant is held in place by wedging itself into the peripheral capsular cul-de-sac. It would be a considerably improvement in implant design if a mechanism for fixating the implant could be obtained while eliminating the need for peripheral haptic members. This would allow for a smaller sized implant, which would be more easily implantable through a smaller incision, and would also minimize ocular irritation after implantation.

SUMMARY OF THE INVENTION

It is an object of the invention to provide an artificial intraocular lens implant and a fixation procedure that does not require peripheral haptic members and does not require the implant to be large for wedging it within the peripheral capsular cul-de-sac. The implant comprises a central optic which is fixated to the posterior capsule by means of an adhesive. The implant comprises a central optic for focusing the light without the need for peripheral haptic members.

The optic may have either peripheral holes for accepting the application of adhesive, or it may contain "wells" which hold adhesive or adhesive materials that can be later activated by the application of additional energy, such as from a laser. This particular approach for implant fixation will allow the implant to be considerably smaller, essentially comprising only of the size of the optic itself. The optic material itself (especially the peripheral optic) may comprise essentially an adhesive or in an pre-adhesive form, such that simple application of energy (such as laser energy) will transform the thermolabile or thermosetting material so that it will adhere the optic to the capsule without the need for an additional adhesive material. The presence of the adhesive, or development of adhesions by means of energy application, provides a reliable and predictable adhesion, making fixation much more immediate, acceptable and reproducible.

The implant of the invention comprises a central optic which includes, contains or receives adhesive material which produces an adhesion between the implant (optic) and the posterior capsule of the human eye after the removal of the human lens. This implant has the advantage of providing a smaller sized implant which is easier to implant and results in less tissue trauma during and after implantation. It also provides for more reliable and reproducible fixation with the means of adhesives or materials which become adhesive. The lens could be placed and fixated on the anterior capsule or the iris of the human eye after extracapsular cataract extraction of the human lens. The implant may have different shapes such as plano-convex, bi-convex, or concavo convex.

DETAILED DESCRIPTION OF THE PREFERRED EMBODIMENTS

Figure 1:
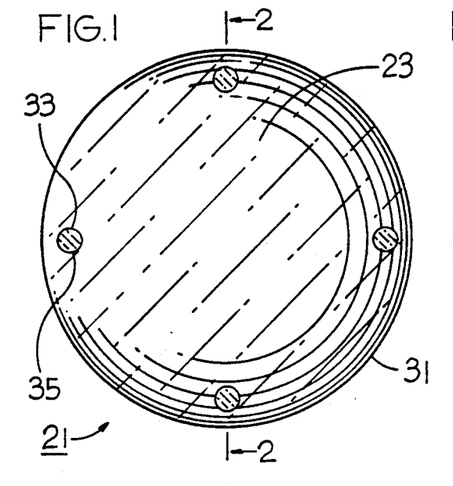
FIG. 1 is a plan view of an artificial intraocular lens of one embodiment of the invention showing its anterior side.
Figure 2:
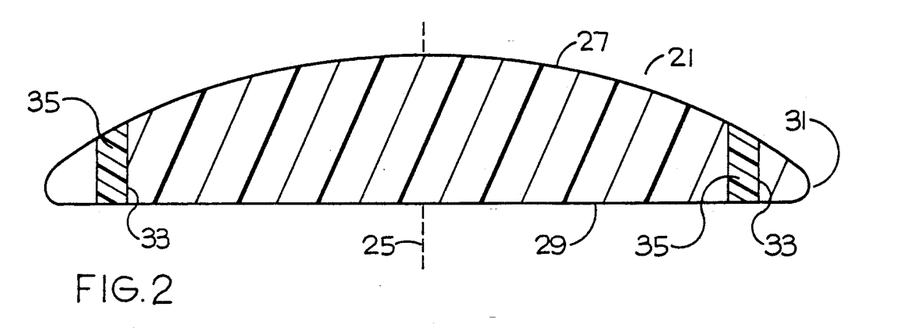
FIG. 2 is an enlarged cross-sectional view of FIG. 1, taken long the lines 2—2 thereof showing the lens as a plano-convex lens.

Referring now to FIGS. 1 and 2, the artificial intraocular lens shown is identified by reference numeral 21 and comprises a transparent optical member 23 having an optical axis 25 and anterior and posterior sides 27 and 29 respectively transverse to the optical axis and extending outward from the optical axis to a peripheral edge of 31. Preferably the lens is circular in shape when seen in a plan view although it could be elliptical, triangular, square or have other shapes. Formed through the lens 21 near the peripheral edge 31 are four spaced apart wells or openings or receptacle sites 33 which extend between sides 27 and 29. Located in the wells 33 is an energy labile (such as thermolabile) adhesive 35. The posterior side 29 of the lens is flat defining a plano-convex optic.

Figure 9:
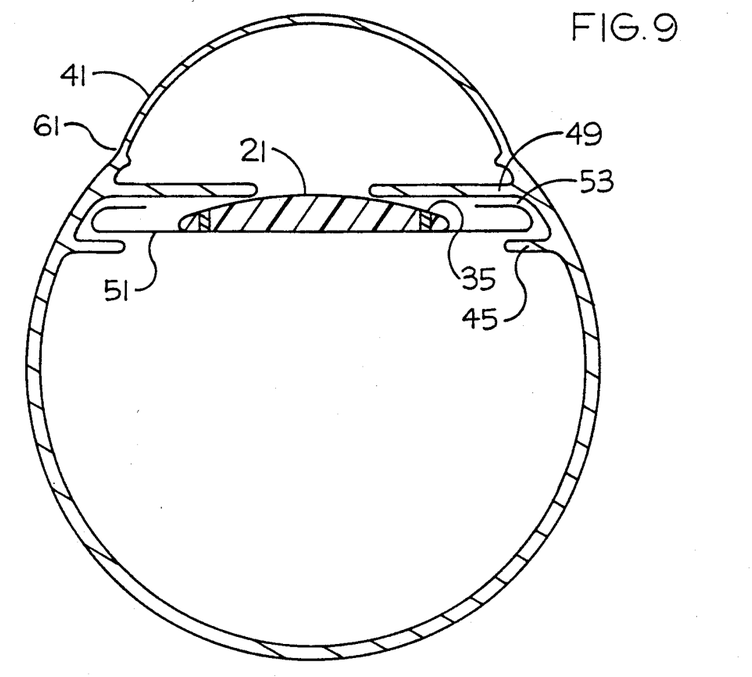
FIG. 9 is a partial cross-sectional view of a human eye having the natural lens removed and the lens of FIG. 2 attached to the posterior capsule.
Figure 10:
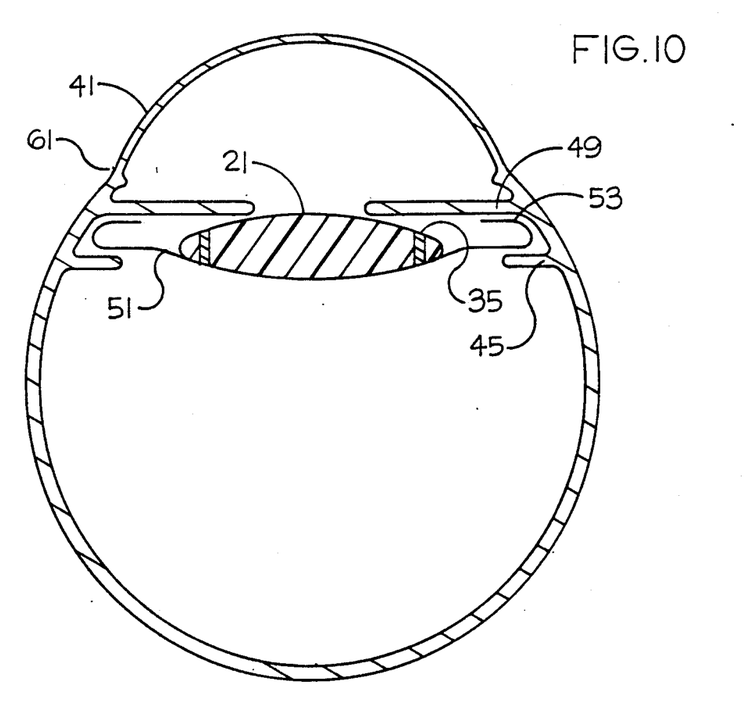
FIG. 10 is a partial cross-sectional view of a human eye having the natural lens removed and the lens of FIG. 6 attached to the posterior capsule.
Figure 11:
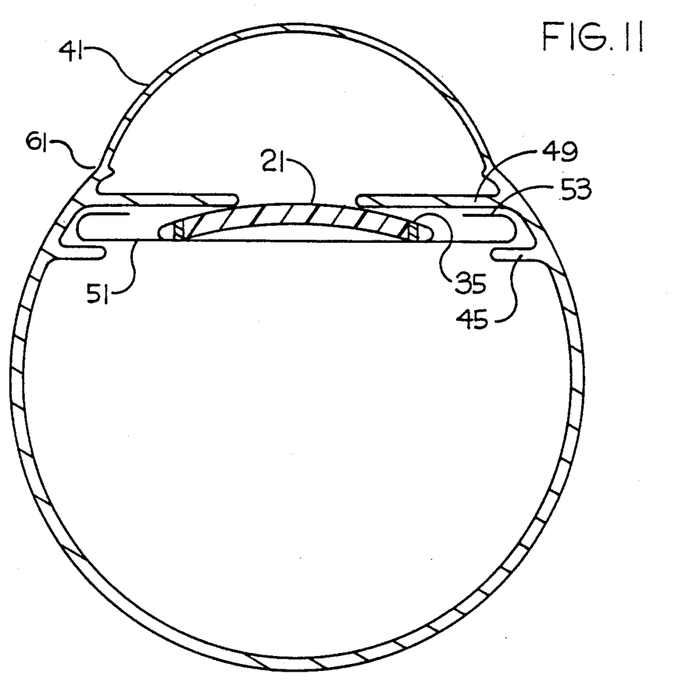
FIG. 11 is a partial cross-sectional view of a human eye having its natural lens removed and the lens of FIG. 7 attached to the posterior capsule.

In FIGS. 9, 10, and 11, the human lens has been surgically removed leaving the transparent posterior capsule 51 and periphery of the anterior capsule 53. In these three figures, reference numerals 41 identify the cornea; 45 the ciliary process; and 49 the iris.

In order to employ a lens 21 of the proper shape and dimensions, pre-measurements will be made of the human eye including the iris to determine the maximum dimensions of the implant lens 21 and the curvature of the anterior and posterior sides 29 of the implant.

In the implantation process, an incision 61 is made through the limbus of the eye to allow removal of the human lens. After removal of the human lens, the implant lens 21 may be inserted through the incision into the eye with the posterior side 29 of the lens 21 seated against the posterior capsule 51 located centrally with respect to the optic axis of the eye. The glue or adhesive precursor 35 in the "wells" 33 is then subjected to a source of energy such as a laser beam from an argon laser, thereby altering the thermolabile glue material causing it to adhere and to adhere the implant lens to the posterior capsule. An ultraviolet (UV) laser may be used to avoid or minimize heating of the adjacent tissue of the eye. This will represent a very localized reaction with virtually no significant damage to the posterior capsule. The wells containing the material 35 may be present in various locations and configurations as is determined optimal for complete and satisfactory fixation of the implant lens 21 to the posterior capsule wherein the implant lens is rendered completely immobile.

Figure 3:
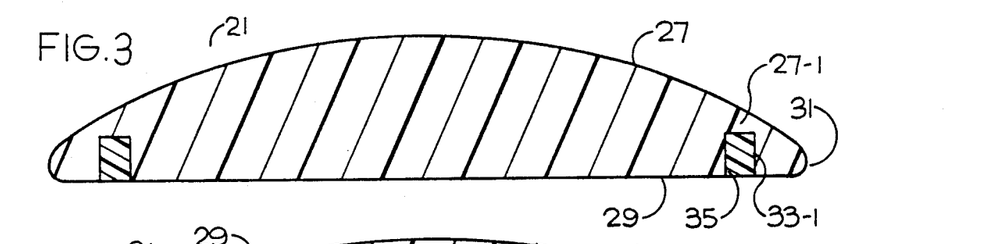
FIG. 3 is an enlarged cross-sectional view of the lens of FIG. 1 showing a modification thereof.

In FIG. 3 the lens 21 of FIGS. 1 and 2 has been modified in that the spaced apart openings or wells 33-1 do not extend completely through the lens but have a thin covering or wall 27-1 on the anterior side to prevent exposure of the glue or adhesive 35 to the iris. In the embodiment of FIG. 3, the openings or wells 33-1 extend from the posterior side of the lens 21 to the wall 27-1. In this embodiment a laser or other energy source also will be employed to cause the material 35 to adhere and to attach the implant lens to the underlying posterior capsule 51. As an alternative, the "wells" 33-1 may have a thin wall on the posterior side of the lens 21. The "wells" 33-1 are filled with the adhesive precursor 35 from the posterior side and the posterior thin walls are energy labile whereby a laser beam may form openings through the posterior thin walls and adhere the material 35 to the lens 21 and to posterior capsule.

Figure 4:
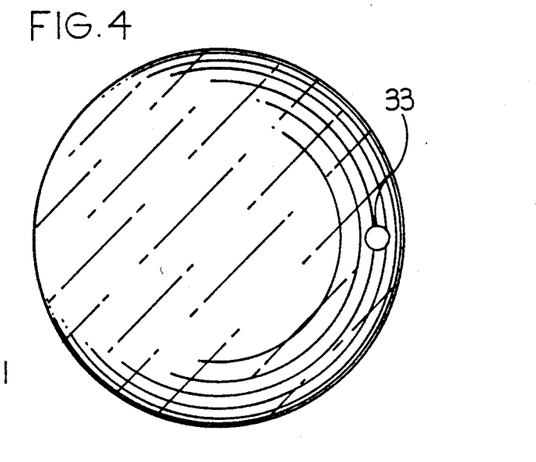
FIG. 4 is a plan view of an intraocular lens of another embodiment of the invention showing its anterior side.

In the embodiment of FIG. 4, the lens 21 has a single opening 33 extending therethrough between sides 27 and 29. The opening has no glue or adhesive precursor therein and after the lens 21 is inserted into the eye through the incision 61, and centered, glue or adhesive 35 in a fluid state is injected to the posterior surface of the lens by way of a small tubular needle of an injection means inserted through the opening 33. The lens 21 then is compressed against the posterior capsule 51.

Figures 5, 8:
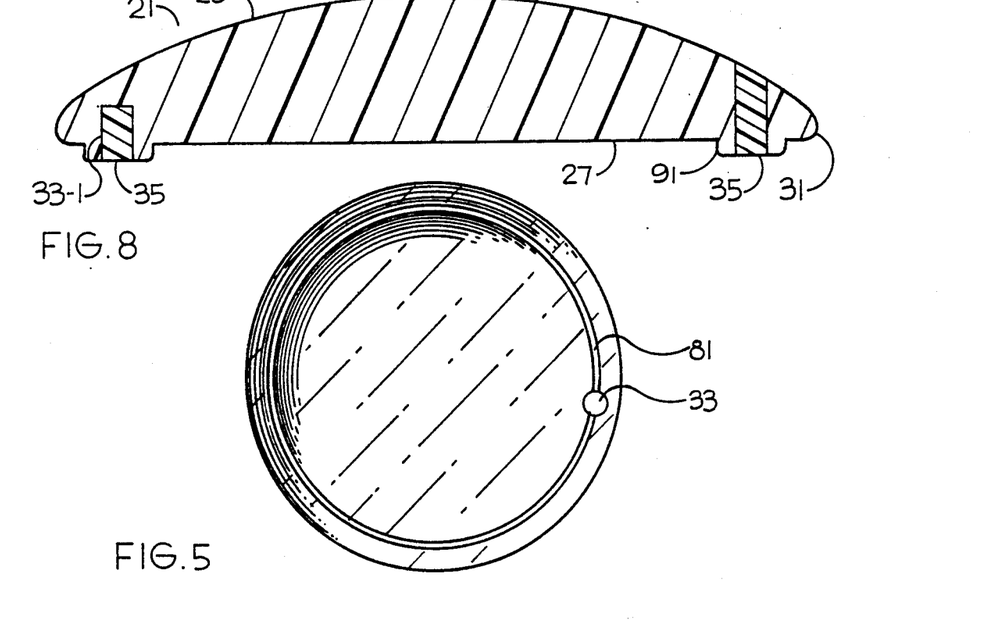
FIG. 5 is a plan view of an intraocular lens of another embodiment of the invention showing its posterior side.
FIG. 8 is a cross-sectional view of an artificial intraocular lens of another embodiment of the invention with "feet" extending from its posterior side.

In the embodiment of FIG. 5 the lens 21 has a single opening 33 extending therethrough between sides 27 and 29 leading to a circular channel 81 formed in its posterior side and employed to guide or direct the adhesive material 35 in a fluid state to its optimal location for fixation. In this embodiment the lens 21 may be inserted through the incision 61 and its posterior side 29 seated against the posterior capsule and the glue or adhesive in a fluid state injected with the injection means and tubular needle into the opening 33 for flow by way of the channel 81 for attaching the posterior side 29 of the lens 21 to the posterior capsule 51. The channel may not be completely circumferential.

Figure 6:
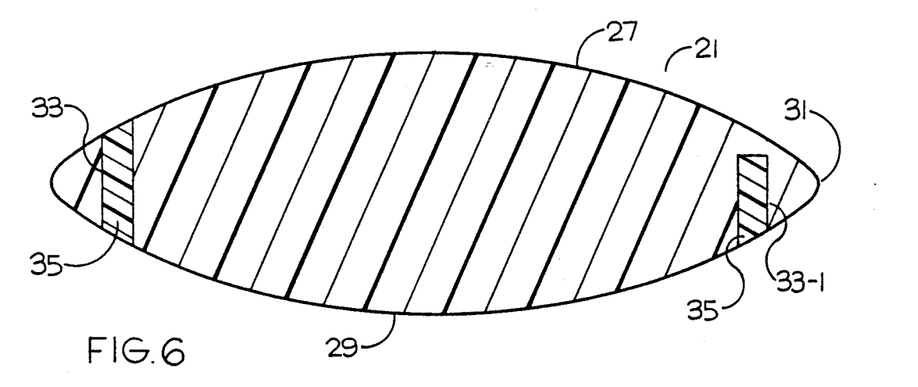
FIG. 6 is a cross-sectional view of an artificial intraocular lens of another embodiment of the invention showing the lens as a bi-convex lens.
Figure 7:
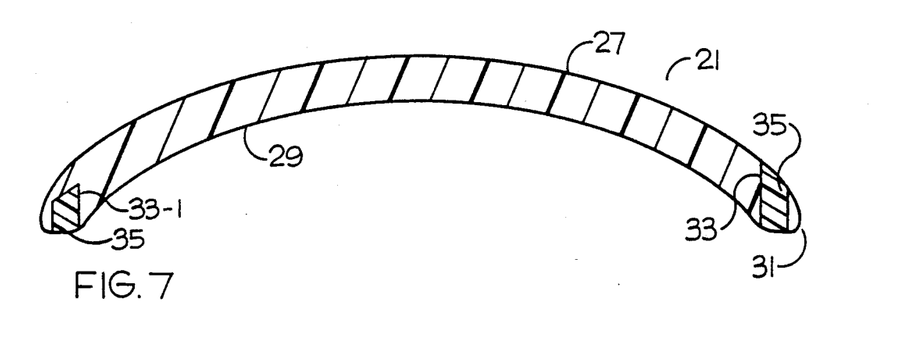
FIG. 7 is a cross-sectional views of an artificial intraocular lens of another embodiment of the invention showing the lens as a meniscus lens.

In FIG. 6 the lens 21 has a convex posterior side 29 and in FIG. 7 the lens 21 has a concave posterior side.

In FIGS. 9, 10, and 11, the lenses of FIGS. 2, 6, and 7 are shown with their posterior sides seated against and attached to the posterior capsule with adhesive. The lens of FIG. 7 will have its central position elevated from the posterior capsule with is posterior side near its peripheral edge seated against and secured to the posterior capsule.

In FIG. 8, the lens 21 has feet 91 extending from its posterior side to elevate its central portion from the posterior capsule.

In FIGS. 6, 7, and 8, the lenses are shown with both the holes 33 from receiving the material 35 and the wells 33-1 filled with material 35, however, it is to be understood that the lenses will have either the holes 33 for receiving the material 35 or the wells 33-1 filled with material 35 (but not both) for use for attachment purposes as desired.

In one embodiment the intraocular lens 21 may be formed of a relatively rigid plastic material such as polymethlmethacrylate (PMMA) to obtain a thinner lens although it could be formed of a flexible plastic material as disclosed in U.S. Pat. No. 4,573,998. Each of the lenses of FIGS. 2, 3, 6, 7 and 8, if round may have a diameter of 6 to 7 mm. The material 35 employed must meet with the necessary and acceptable standards for adequate permanent bonding with intraocular biocompabilty and may be a cyanoacrylate glue or suitable silicone adhesive for a lens 21 formed of PMMA. A suitable cyanoacrylate glue which is non-biodegradable and which will bond the intraocular lens to the tissue of the eye for a number of years (at least up to five years), and possibly permanently, is N-octyl-2-cyanoacrylate. This adhesive will be used in small amounts and will be employed to bond the intraocular lens to either the anterior or posterior capsule of the eye, and possibly to the front side of the iris. Implantation and bonding will be managed to prevent contact of this adhesive with the cornea to prevent any problems of tissue toxicity with respect to the cornea. In the implantation and bonding process of the implant lens to the anterior or posterior capsule, this adhesive will be controlled to be located only between the implant and the anterior or posterior capsule, avoiding contact with other tissues such as the cornea. In this bonding process, there is no healing involved and the natural inflammatory process associated with healing is not involved in adhering an implant to the anterior or posterior capsular surface of the human eye.

N-octye-2-cyanoacrylate is activated upon contact with moisture. A lens having apertures 33 formed completely therethrough may be used and the adhesive injected through the apertures with a hollow needle. If the lens has the wells 33-1 formed therein, the wells 33-1 will be filled with the adhesive and the openings of the wells covered with a material that will be dissolved by moisture of the eye such as hydroxyethyl cellulose, hydroxypropyl cellulose, polysaccharides, polyethylene oxide, or polypropylene oxide..

When a laser beam is employed to adhere the implant to the human tissue, the glue or adhesive material may be a thermoplastic or thermosetting material.

The procedure for implantation of the implant is a microsurgical procedure requiring the use of an operating microscope. Anesthesia suitable for this procedure may be either general endotracheal or local anesthesia (such as retrobulbar or periocular local anesthetic injection), which are commonly used for other routine types of intraocular surgery, such as cataract extraction. Similarly, the sterile technique and surgical principles involved are those customarily used routinely for intraocular surgery, such as cataract extraction.

The implantation technique for the intraocular lens fixated to the posterior capsule with adhesive is as follows:

Preoperative pupillary dilation is necessary and can be accomplished with several topical mydriatic medications, such as Mydriacyl 1%, Cyclogyl 1% or Neosynephrine 10%. Typically, a preoperative regimen consists of 1 drop of Cyclogyl 1% and 1 drop of Neosynephrine 10%, each medication being instilled in the operative eye a total of 3 times, the instillations being separated by about 5 minutes. The instillations should be completed approximately one-half hour prior to surgery.

After preoperative dilation has been accomplished, the patient is positioned under the operating microscope, and the eyelid is separated with an eyelid speculum. An incision through the surgical limbus, similar to that performed in cataract surgery, will provide both a means of removal of the cataract and also a site through which introduction of the implant into the eye will be accomplished. The usual location for the incision is in the 12 o'clock position, but other limbal locations may be selected during the particular case. A fornix based conjunctival flap is to made expose the underlying limbus in preparation for the limbal incision, and the limbal area is cleaned and hemostasis is achieved. A usual cataract-type of multiplaned limbal incision (commonly a bi-planned incision) is made at the surgical limbus. An initial partial thickness corneoscleral incision is made with a scalpel, after which the anterior chamber is entered through the partial thickness incision with a scalpel. The incision is widened and completed with corneoscleral scissors. The anterior chamber typically is filled with a viscoatelastic material, such as Healon or Occucoat. A sharp cystitome is used to make an anterior capsulotomy is either the "can-opener style" or a smooth tear capsulorhexsis. The anterior capsule is then removed allowing access to the cataract. The central nuclear material is removed, either by expression through the previously made limbal wound with appropriately placed ocular pressure or alternately by phacoemulsification. The remaining cortical material is removed with irrigation and aspiration. The capsular bag is then left intact with the posterior capsule and the peripheral portion of the anterior capsule still in place. The intraocular lens is then introduced into the eye through the limbal incision and is placed within the capsular bag, aligning the implant with the optic axis of the eye. The implant is placed firmly against the posterior capsule where contact is made particularly with the periphery of the implant, which essentially consists of an optic. Prior to implantation, it is necessary to establish and maintain the anterior chamber with an air bubble, physiologic balanced salt solution, or possibly with viscoatelastic material.

Once the implant has been positioned on the posterior capsule (or alternatively on the anterior capsule or the iris) and then centered, it then remains to make the implant adherent to the underlying anterior capsule. This is accomplished by injection of the adhesive through the needle into the appropriate openings, which are integral to the implant and are designed to accept and direct the liquid adhesive material to the desired location. An alternative technique is that the adhesive may be directly injected between the implant and the lens capsule to provide the adhesion. The adhesive used in this manner (such as a Cyanoacrylic type of glue) is in a liquid form and develops the adhesion bond after injection. The adhesive should be used as minimally as possible, and should primarily be used in the periphery to render the peripheral aspect of the implant adherent. The adhesive should not generally be used in the central optic axis area since this might interfere with the optics of the implant.

A second type of adhesive material may be employed as indicated previously, this being a thermoplastic or a thermosetting type of adhesive material which becomes activated and develops its adhesive bond upon the application of energy, such as heat or light energy particularly. This type of adhesive material is located, for the same reasons as stated above, in the periphery of the implant in the wells or as an integral part of the implant design. The energy source is then directed and delivered to the site of the adhesive material where it is activated, and the adhesive bond between the epiphakic implant and the underlying posterior capsule is produced. Various sources of energy for adhesive activation may be employed. The laser is a particularly suitable source because of its ability to deliver a variable, well controlled, and intensive amount of energy to a small and discrete area. Depending upon a particular configuration of a laser delivery system, the energy may be directed and delivered from a source external to the eye (possibly mounted on and delivered through the operating microscope), or through an instrument tip introduced into the eye. In the case of a probe tip introduced into the eye for energy delivery, the tip may need to be placed directly in contact with or possibly only in close proximity to the adhesive material to be activated. That is to say, the tip may need to be directly physically in contact with adhesive material in order to deliver sufficient energy for bonding. The probe tip energy source may not need to come in contact with the implant or adhesive in all cases, but may provide sufficient energy from a small distance away from actual contact with the implant and its adhesive. As mentioned, a possible very suitable location for a laser source is attached to and working in conjunction with the operating microscope, which serves as its general guide for positioning. Activation of the laser or a probe tip is accomplished by switch control by the operating surgeon. Several spots or sites of adhesive bonding may be necessary to provide adequate adhesion and fixation of the implant to the underlying capsule. Therefore, several sites of energy application, or adhesive injection as the case may be, may be necessary around the peripheral aspect of the implant. These bonding locations at the periphery of the implant will be roughly circular or arcuate in shape, and basically will conform to the general circular curvature of the implant periphery. As a general principle, the amount of adhesive material used, the number of bonding sites employed, and the amount of bonding energy used (for example, if a laser system is utilized) should all be kept to the minimum optimally necessary to accomplish satisfactory bonding and stable fixation. Also, as mentioned previously, it is desirable to avoid adhesive in the optic axis area of the eye if at all possible.

Once the sites of adhesive bonding are accomplished, and it is felt that the implant is suitably and satisfactorily fixated, the incision is closed in the standard method using surgical suture techniques common to cataract surgery. The anterior chamber is evacuated of the previously placed viscoatelastic material or air bubble, as is the surgeon's desire. The eye is then patched in the usual fashion to intraocular surgery. The procedure is then complete.

In another embodiment, the implant lens 21 may have a peripheral and surrounding edge or rim which is energy labile, and upon being subjected to a localized energy source such as heat from an Argon laser beam or energy from a UV laser, transforms itself into an adhesive which then becomes adherent and bonds to the underlying human lens capsule.

In addition, the peripheral edge of the lens may be designed with "feet" or structures to elevate the central body of the implant lens off the capsule (FIG. 8). One purpose of the feet is to allow the elevation of the lens off of the adjacent posterior capsule to facilitate laser capsulotomy, posteroperatively. This same elevation off the posterior capsule is accomplished with the meniscus-style of optic configuration (FIG. 7). Modern technology will also make possible the development of multiple strength bifocal and multifocal optics for the correction of presbyopia, either alone or in conjunction with the correction of hyperopia or myopia as is currently being investigated in the optics of intraocular implants used after the removal of a cataract. Also, the correction of astigmatism may be possible.

Figure 13:
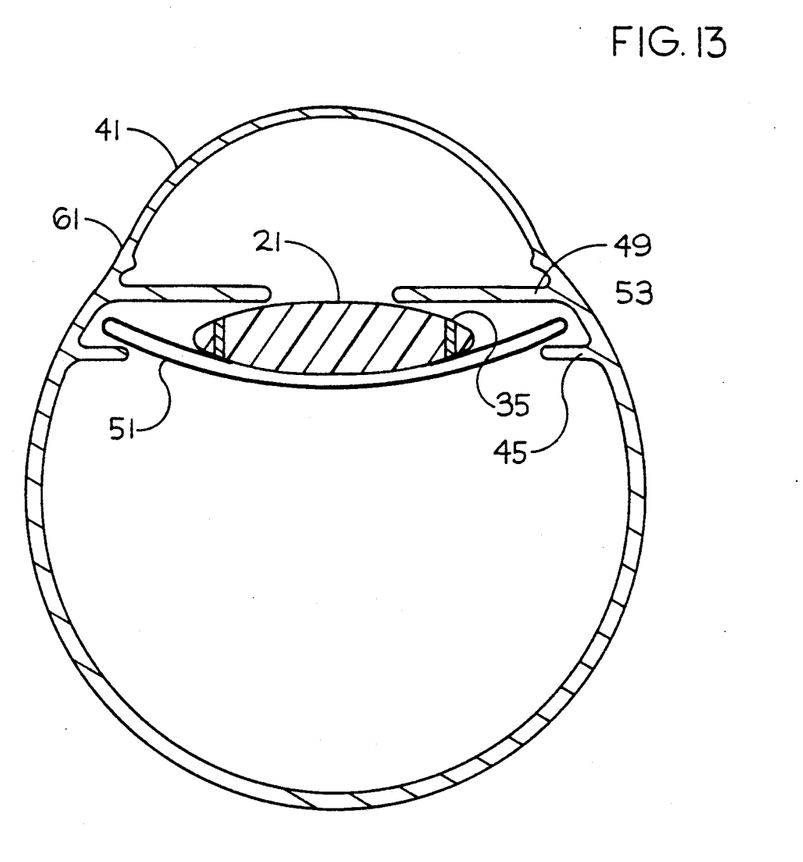
FIG. 13 is a cross-sectional view of a bi-convex artificial intraocular lens shown attached to the anterior capsule by adhesive.

As mentioned above, the implant lens may be secured by adhesive to the anterior capsule 53 or to the iris after removal of the human lens. Either of the lenses of FIGS. 2, 3, 6, 7 or 8 may be attached to the anterior capsule or the iris. In attaching the implant lens to the anterior capsule, its remaining peripheral edges may be folded against the posterior capsule 51 as shown in FIG. 13, and the lens attached by the adhesive to the anterior side of the anterior capsule edge. In the alternative, the lens may be bonded to the back surface of the peripheral edge of the anterior capsule. The central aperture through the anterior capsule may be 4-5 mm in diameter such that there will be enough peripheral area for allowing a 6-7 mm diameter lens to be seated against and attached thereto. Thus the lens implant may be attached with adhesive to the capsular membrane or bag to either the posterior capsule 51 or the anterior capsule, although preferably it will be attached to the posterior capsule 51.

Figure 12:
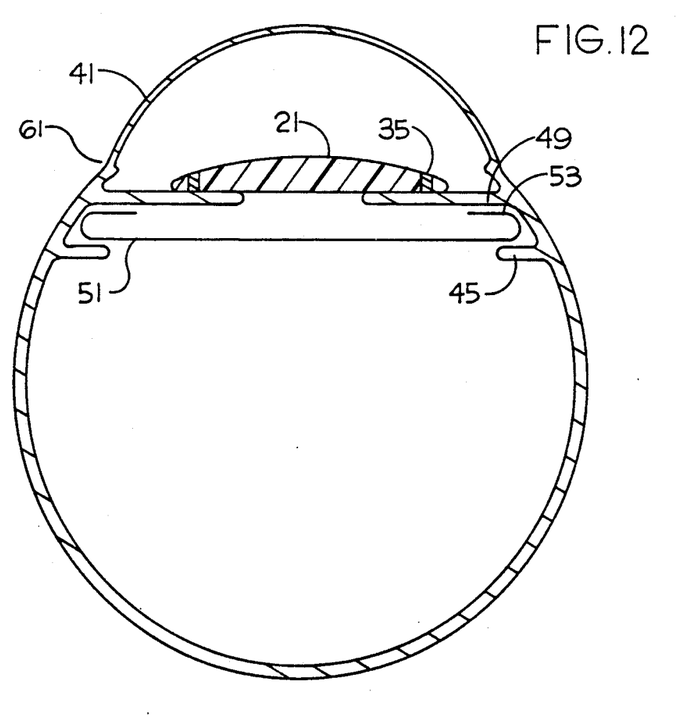
FIG. 12 is a partial cross-sectional view of a human eye having its natural lens removed and the lens of FIG. 2 attached to the anterior side of the iris.

Any of the lens implants of FIGS. 2, 3, 6, 7, or 8 may be attached to the iris 49 with adhesive after removal of the human lens. FIG. 12 shows the lens implant of FIG. 2, attached to the anterior side of the iris 49 with adhesive. Attachment is at the mid-periphery of the iris.

Although the process above relates to removal of the human lens and immediately thereafter attaching an artificial lens implant to the capsular membrane or to the iris with adhesive, it is to be understood that the process of attaching the implant lens to the capsular membrane or iris with adhesive may be employed upon removal of a previously implanted artificial intraocular lens which was previously implanted upon removal of the human lens.

In addition, it is to be understood that a suitable implant lens could be attached by adhesive to the anterior side of the iris with the human lens still in place to correct for nearsightedness, farsightedness, stigmatize or presbyopia. The implant lens will be suitable designed for correcting for either of the above four deficiencies and may have the openings 33 or wells 33-1 for receiving adhesive for allowing the lens to be attached to the anterior side of the iris by using liquid adhesive or laser energy.

A UV laser may be used in the process of bonding an artificial intraocular lens to the capsular membrane or iris of the eye. This embodiment uses a photoinitiator and an acryllic monomer. Upon stimulation by appropriate energy from a source such as a laser (for example as a UV laser), the photoinitiator then brings about the polymerization of the acrylic monomer resulting in an adhesive bond between the implant and the tissue.

Figure 14:
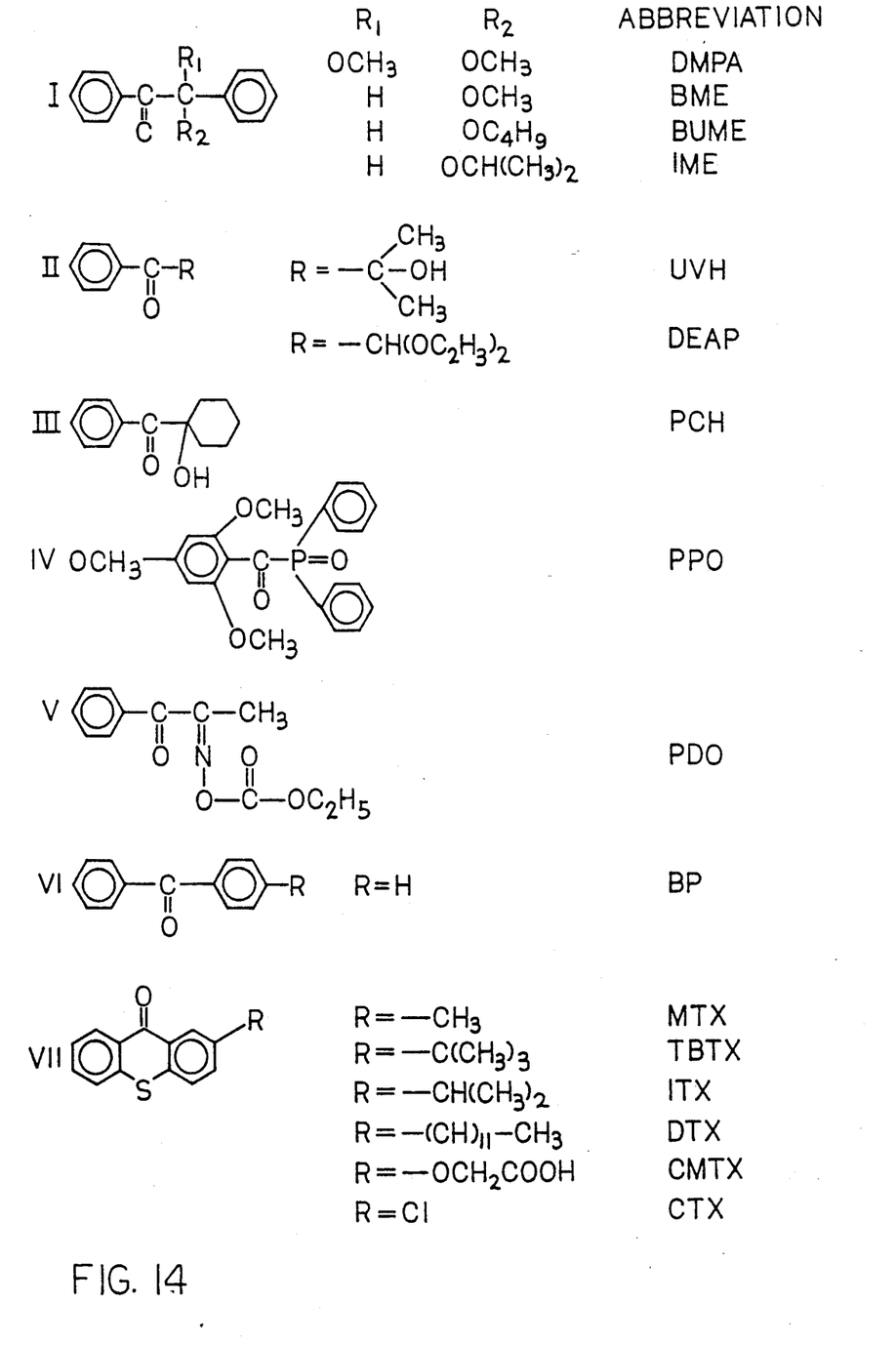
FIG. 14 illustrates examples of photoinitiators.

Shown in FIG. 14 are different examples of photoinitiators.

I claim:

1. A method of implanting an artificial intraocular lens into a human eye from which the natural lens has been removed leaving the capsular membrane, comprising the steps of:
   providing an artificial intraocular lens,
   inserting said artificial intraocular lens into the eye,
   seating said artificial intraocular lens against the capsular membrane of the eye in substantial optical alignment therewith, and,
   attaching said artificial intraocular lens to the capsular membrane of the eye with the use of a material capable of being converted to an adhesive,
   said attachment step being carried out by introducing said material into the eye and applying energy to said material to convert it to an adhesive to bond said intraocular lens to the capsular membrane of the eye.

2. The method of claim 1, wherein:
   said artificial intraocular lens is seated against and attached to the posterior capsule of the eye with said adhesive.

3. The method of claim 1, wherein:
   said artificial intraocular lens is seated against and attached to the remaining peripheral edge of the anterior capsule of the eye with said adhesive.

4. The method of claim 1, wherein:
   the energy applied to said material to convert it to an adhesive, comprises laser energy.

5. The method of claim 2, wherein:
   the energy applied to said material to convert it to an adhesive, comprises laser energy.

6. The method of claim 3, wherein:
   the energy applied to said material to convert it to an adhesive, comprises laser energy.

7. A method of implanting an artificial intraocular lens into a human eye, comprising the steps of:
   providing an artificial intraocular lens into the eye,
   seating said artificial intraocular lens against the anterior surface of the iris of the eye in substantial optical alignment therewith, and
   attaching said artificial intraocular lens to the anterior surface of the iris of the eye with a material capable of being converted to an adhesive,
   said attachment step being carried out by introducing said material into the eye and applying energy to said material to convert it to an adhesive to bond said intraocular lens to the iris of the eye.

8. The method of claim 7, wherein:
   the energy applied to said material to convert it to an adhesive, comprises laser energy.

* * * * *